(12) United States Patent  (10) Patent No.: US 7,775,715 B2
Warner et al.  (45) Date of Patent: Aug. 17, 2010

(54) METHOD OF CALIBRATION FOR COMPUTED TOMOGRAPHY SCANNERS UTILIZED IN QUALITY CONTROL APPLICATIONS

(75) Inventors: Rodney H. Warner, Austin, TX (US); Edwin L. Strickland, III, Austin, TX (US); Henry W. Sikorski, East Granby, CT (US)

(73) Assignee: United Technologies Corporation, Hartford, CT (US)

( * ) Notice: Subject to any disclaimer, the term of this patent is extended or adjusted under 35 U.S.C. 154(b) by 90 days.

(21) Appl. No.: 12/199,826

(22) Filed: Aug. 28, 2008

(65) Prior Publication Data

US 2010/0054396 A1 Mar. 4, 2010

(51) Int. Cl.
*G01N 23/083* (2006.01)
*G01D 18/00* (2006.01)
(52) U.S. Cl. ............................... 378/207; 378/4; 378/20
(58) Field of Classification Search ............... 378/4, 378/20, 207
See application file for complete search history.

(56) References Cited

U.S. PATENT DOCUMENTS

| 4,233,507 | A |  | 11/1980 | Volz |  |
|---|---|---|---|---|---|
| 4,782,502 | A |  | 11/1988 | Schulz |  |
| 4,985,906 | A |  | 1/1991 | Arnold |  |
| 5,799,059 | A |  | 8/1998 | Stembridge |  |
| 6,909,768 | B2 | * | 6/2005 | Takagi et al. | 378/4 |
| 7,056,021 | B2 | * | 6/2006 | Tsujii | 378/207 |
| 7,147,373 | B2 | * | 12/2006 | Cho et al. | 378/207 |
| 2008/0075227 | A1 | * | 3/2008 | Christoph et al. | 378/23 |
| 2008/0084962 | A1 | * | 4/2008 | Zhang et al. | 378/57 |
| 2008/0279342 | A1 | * | 11/2008 | Holt | 378/207 |

OTHER PUBLICATIONS

U.S. Appl. No. 12/037,381, filed Feb. 26, 2008.
U.S. Appl. No. 12/112,521, filed Apr. 30, 2008.
U.S. Appl. No. 12/037,302, filed Feb. 26, 2008.
U.S. Appl. No. 12/112,565, filed Apr. 30, 2008.
U.S. Appl. No. 12/099,899, filed Apr. 9, 2008.
U.S. Appl. No. 12/043,371, filed Mar. 6, 2008.

* cited by examiner

*Primary Examiner*—Edward J Glick
*Assistant Examiner*—Thomas R Artman
(74) *Attorney, Agent, or Firm*—Carlson, Gaskey & Olds

(57) ABSTRACT

A method of calibrating a computed tomography system includes the steps of mounting a scan geometry defining tool on a rotating object positioning unit of a computer tomography scanner. The scan geometry defining tool has structure of precisely measured dimensions. A beam is directed from an x-ray source of the computed tomography system through the structure of the scan geometry defining tool. A detected image after absorption of the x-ray from the scan geometry defining tool is analyzed, and utilized to determine a distance from the x-ray source spot location to the center of rotation of the object positioning unit. A beam is also directed from the x-ray source through a system performance test standard tool and analyzes a number of electronic and computer performance characteristics. The analyzed characteristics can be compared to expected characteristics to provide feedback on the operation of electronic and computer functions within the computed tomography system.

15 Claims, 2 Drawing Sheets

METHOD OF CALIBRATION FOR COMPUTED TOMOGRAPHY SCANNERS UTILIZED IN QUALITY CONTROL APPLICATIONS

BACKGROUND OF THE INVENTION

This application relates to a method of calibrating a computed tomography scanner that will be utilized in checking the tolerance ranges on manufactured components.

Computed tomography scanners are utilized in a number of applications. Essentially, x-rays are passed through a part, and onto a highly collimated detector array. A signal from the array is then provided to an image analysis computer from the detector array.

Computed tomography scanners have been widely utilized in various medical applications. More recently it has been proposed to utilize such scanners in quality control applications such as checking tolerances of manufactured components. However, such applications require close calibration of the equipment for performing the scanning. To date, adequate calibration methods have not been developed.

SUMMARY OF THE INVENTION

A method of calibrating a computed tomography system includes the steps of mounting a scan geometry defining tool on a rotating object positioning unit of a computer tomography scanner. The scan geometry defining tool has structure of precisely measured dimensions. A beam is directed from an x-ray source of the computed tomography system through the structure on the scan geometry defining tool. A detected image after absorption of the x-ray by the scan geometry defining tool is analyzed, and utilized to determine the distance from an x-ray source to the center of rotation of the object positioning unit. A beam is also directed from the x-ray source at a system performance monitoring tool and analyzes a number of electronic and computer performance characteristics are determined, and compared to expected characteristics to provide feedback on the operation of electronic and computer functions within the computed tomography system.

These and other features of the present invention can be best understood from the following specification and drawings, the following of which is a brief description.

DETAILED DESCRIPTION OF THE PREFERRED EMBODIMENT

Figure 1:
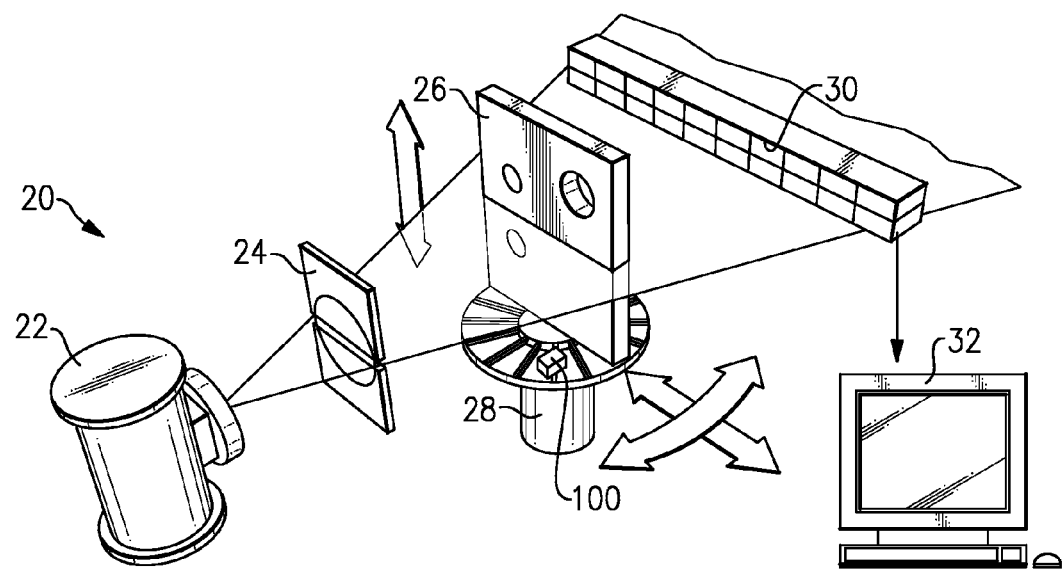
FIG. 1 shows a schematic view of computed tomography inspection station.

A system 20 for providing computed tomography inspections of a component 26 is illustrated in FIG. 1. As shown, an x-ray source, which may be a 450 KeV x-ray source, directs x-rays through a source collimation element 24, and through the component 26. An object positioning unit 28 rotates the component 360 degrees. A highly collimated discrete detector array 30 samples the x-ray absorption by the component 26. A computer 32 is provided with appropriate image analysis software, and can reconstruct an image with an accurately known geometric scale from the x-ray absorption data and positional information. Scaled images may be utilized to measure wall thicknesses by defining the pixels that are at a threshold that is half air and half material. The use of the system to provide such tolerance measurements is known.

Figure 2:
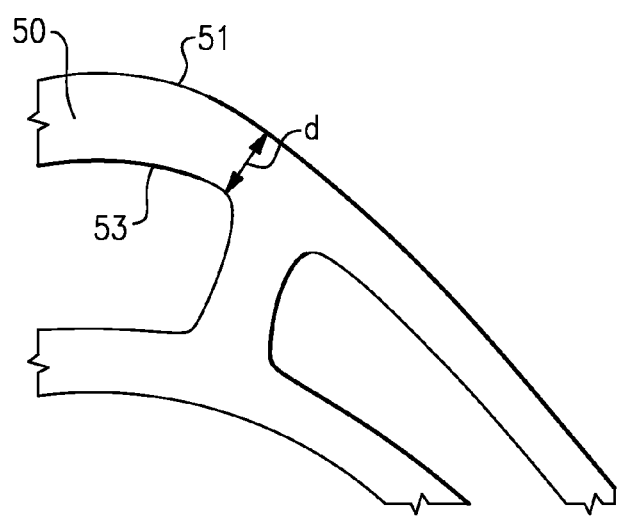
FIG. 2 shows an image developed by a computed tomography scanner.

One application which shows promise is checking the thicknesses of walls such as in a turbine blade 50 for a gas turbine engine. As shown in FIG. 2, a wall thickness d between an outer wall 51 and an inner wall 53 can be electronically measured by the image analysis computer. However, to ensure the detected images are reliable, calibration of the equipment to accurately define image scale is required.

Figure 3:
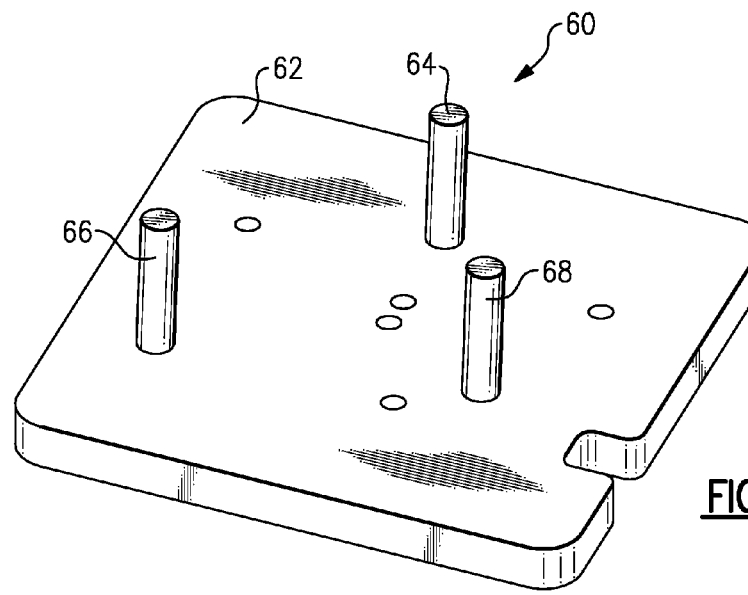
FIG. 3 shows a first calibration component.

FIG. 3 shows a source to center of rotation distance (SRAD) setup, or scan geometry defining tool 60. As shown, a base 62 includes three pins 64, 66 and 68. The pins are positioned at known locations relative to each other and are accurately measurable. Calibration or measurement of the scan geometry defining tool must be performed by a technique traceable to National Institute of Standards and Testing (NIST) calibration standards. Recalibration of the tool must be performed at a defined period per an established technique. In one application the pins are precision machined 0.375 inch diameter pins in a triangular pattern with unequal length distances between pin centers.

The tool 60 is mounted on an object positioning unit 28 of a computed tomography scanner which is to be calibrated. The purpose of the tool 60 is to calibrate the distance from the center of rotation of the object positioning unit 28 to the of the x-ray source spot. The tool 60 is placed on an object positioning unit 28 at a known location and scanned at established parameters. The scan data is reconstructed into a scaled image. Image analysis software is used to "crawl" around each of the pins 64, 66 and 68, and find a center of each pin. Distances between pins 64-68, 64-66 and 66-68 are all determined. Once these image derived distances are known, and are associated with an assumed center of rotation in the object positioning unit 28, then the distance from that center of rotation to the location of an x-ray source spot can be determined. This distance can be utilized to adjust image geometry calculations during the machine's operation.

This calibration may not be performed every day. In one application, the calibration with the tool 60 could be performed once a month, as an example. On the other hand, the calibration can be performed more frequently if drift is suspected in the scanner.

Figure 4:
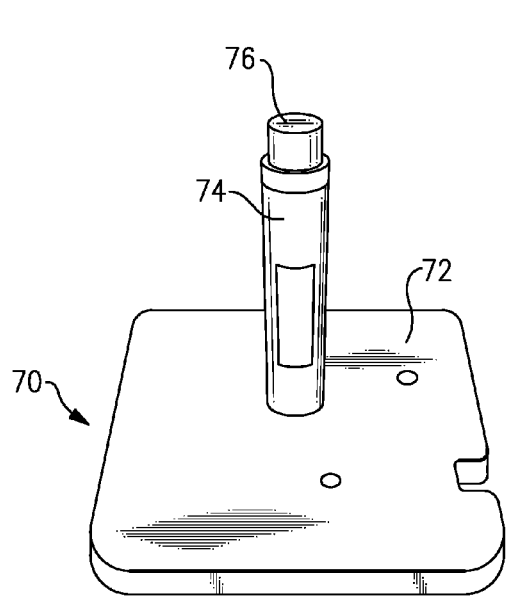
FIG. 4 shows a second calibration component.
Figure 5:
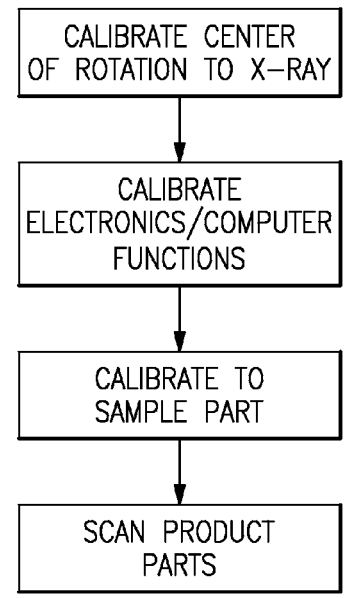
FIG. 5 is a flowchart of the inventive method.

A second tool 70 is shown in FIG. 4. This is a system performance standard, which may be a 0.750 inch diameter metal object which is located off a center of objection rotation. The tool's diameter should be accurately measurable. The tool 70 may have a support pin 74 carrying a metal disk 76 of a known size. Calibration or measurement of the System Performance standard tool must be performed by a technique traceable to National Institute of Standards and Testing (NIST) calibration standards. Recalibration of the tool must be performed at a defined period per an established technique. This tool is utilized to calibrate electronic and computer control over various characteristics.

The system performance test standard 70 is placed on the object positioning unit 28, and scanned. Then, various system performances indicators are checked against inspected indicators.

As an example, signal to noise ratio is checked against a standard. Signal to noise ratio is the image density of pixels in the central thirty percent diameter of the disk, divided by a standard deviation of the pixels' density value within the circle.

A diameter measurement of the disk 76 is checked against an diameter measurement as determined by tool calibration for accuracy of the overall machine performance.

Sharpness can be defined as an average gradient in the image of the pixels at the edge of the disk in a two pixel width wide band centered on the outer edge of the pixels with a density at a half-air and half disk material density threshold. This is a measurement of image sharpness relative to the trend of other images of the same standard taken with the same nominal image perimeters. A higher valve would indicate a sharper image.

The image sharpness is also checked against inspected standards with a full width half max test. The full width half max test is obtained by geometrically transforming the image of the disk into polar coordinates centered on the disk's center in the image. A gradient of the polar-coordinates image is then calculated, and is smoothed parallel to the circumference of the disk to reduce random pixel-to-pixel noise. The width of the edge-gradient is measured at half the density value of the maximum of the gradient and is divided by two to give the value it would have in Cartesian coordinates. This number is a quantitative estimate of the resolution of the image data.

Features in the computed tomography slice plane which are substantially larger than the resolution value resolved, and features which are substantially smaller than this value are not resolved, and will be seen at low contrast, if at all. Resolution values may be returned in both millimeters and inches. Lower resolution values would indicate a sharper image.

In addition, x-ray and filtration performance is determined with by the beam hardening coefficient. The beam hardening coefficient is a metal density value near the outer edge of the disk divided by the metal density value in a circle at the center of the disk, within thirty percent of the radius of the disk radius. Beam hardening effects reduce the apparent density at the center of the disk related to the density at the outer edge.

The system performance test standard 70 need not be utilized every day either, but may be utilized periodically to check the electronic and computer performance of the system.

Other calibration techniques that may be utilized include the use of an object of the same geometry, material and process as the components 26 to be scanned. As an example, a sample turbine blade having known dimensions may be utilized at the beginning and end of each shift to look for creep or drift in calibration.

In addition, a scan reference standard, which may be a tube of the same material and process as the components to be scanned, with a wall thickness similar to the components scanned thickness may be utilized in every computed tomography process performed. As an example, the tube can be mounted on the object positioning unit 28 adjacent to the component 26 to be scanned. The tube can be checked against the expected size of the tube, and the result with regard to the component which is being scanned may only be accepted if the tube is scanned to be within an expected range. A tube 100 to be scanned for these reasons is shown schematically in FIG. 1.

Finally, as a final check on calibration, some components, such as turbine blades, which have been scanned by the computed tomography process may be cut up and measured by some other process to determine if the computed tomography results are accurate.

The above methods are but one method of calibrating the computed tomography equipment. In general, a computer tomography calibration method which initially identifies a distance between a center of rotation and to an x-ray spot, and then also calibrates with regard to electronic and computer standards, but doing so with different parts than those specifically disclosed, may still come within the scope of this invention.

It should be noted that a computing device can be used to implement various functionality, such as that attributable to the computer 32 depicted in FIG. 1. In terms of hardware architecture, such a computing device can include a processor, memory, and one or more input and/or output (I/O) device interface(s) that are communicatively coupled via a local interface. The local interface can include, for example but not limited to, one or more buses and/or other wired or wireless connections. The local interface may have additional elements which are omitted for simplicity, such as controllers, buffers (caches), drivers, repeaters, and receivers to enable communications. Further, the local interface may include address, control, and/or data connections to enable appropriate communications among the aforementioned components.

The processor may be a hardware device for executing software, particularly software stored in memory. The processor can be a custom made or commercially available processor, a central processing unit (CPU), an auxiliary processor among several processors associated with the computing device, a semiconductor based microprocessor (in the form of a microchip or chip set) or generally any device for executing software instructions.

The memory can include any one or combination of volatile memory elements (e.g. random access memory (RAM, such as DRAM, SRAM, SDRAM, VRAM, etc.)) and/or nonvolatile memory elements (e.g., ROM, hard drive, tape, CD-ROM, etc.). Moreover, the memory may incorporate electronic, magnetic, optical, and/or other types of storage media. Note that the memory can also have a distributed architecture, where various components are situated remotely from one another, but can be accessed by the processor.

The software in the memory may include one or more separate programs, each of which includes an ordered listing of executable instructions for implementing logical functions. A system component embodied as software may also be construed as a source program, executable program (object code), script, or any other entity comprising a set of instructions to be performed. When constructed as a source program, the program is translated via a compiler, assembler, interpreter, or the like, which may or may not be included within the memory.

the Input/Output devices that may be coupled to system I/O Interface(s) may include input devices, for example but not limited to, a keyboard, mouse, scanner, microphone, camera, proximity device, etc. Further, the Input/Output devices may also include output devices, for example but not limited to, a printer, display, etc. Finally, the Input/Output devices may further include devices that communicate both as inputs and outputs, for instance but not limited to, a modulator/demodulator (modem; for accessing another device, system, or network), a radio frequency (RF) or other transceiver, a telephonic interface, a bridge, a router, etc.

When the computing device is in operation, the processor can be configured to execute software stored within the memory, to communicate data to and from the memory, and to generally control operations of the computing device pursuant to the software. Software in memory, in whole or in part, is read by the processor, perhaps buffered within the processor, and then executed.

A worker of ordinary skill in the art would recognize that certain modifications would come within the scope of this invention. For that reason, the following claims should be studied to determine the true scope and content of this invention.

What is claimed is:

1. A method of calibrating a computed tomography system including the steps of:
mounting a scan geometry defining tool on a rotating object positioning unit of a computer tomography scanner, said scan geometry defining tool having structure at a known location relative to a center of rotation of the object positioning unit;
directing a beam from an x-ray source of the computed tomography system through the structure of the scan geometry defining tool, analyzing a detected image after absorption of the x-ray from the scan geometry defining tool, and utilizing said analyzed image to determine a distance from an x-ray location to the center of rotation of the object positioning unit;
directing a beam from the x-ray source at a system performance test standard tool and analyzing a number of electronic and computer performance characteristics, and comparing the analyzed characteristics to expected characteristics to provide feedback on the operation of electronic and computer functions within the computed tomography system; and
said electronic and computer control characteristics including at least one of beam hardening, a signal to noise ratio feedback, a measured size of a portion of said system performance test standard tool, and measured sharpness and resolution of a detected image.

2. The method as set forth in claim 1, wherein distinct tools are utilized as the scan geometry defining tool and the system performance test standard tool.

3. The method as set forth in claim 2, wherein a single tool is utilized to provide the electronic and computer control characteristics.

4. The method as set forth in claim 1, wherein said electronic and computer control characteristics include each of beam hardening, a signal to noise ratio feedback, a measured size of a portion of said system performance test standard tool, and measured sharpness and resolution of a detected image.

5. The method as set forth in claim 1, wherein standard components which are of the same material and general geometry of actual components to be scanned are periodically scanned and the results compared to known results to further provide feedback on the calibration of the computer tomography system.

6. The method as set forth in claim 1, wherein a standard size element is positioned on the object positioning unit along with a component to be scanned, and the standard size element is utilized to provide further feedback on the accuracy of the information provided by the computed tomography system with regard to the component to be scanned.

7. The method as set forth in claim 1, wherein the scan geometry defining tool includes a plate which is to be positioned on the object positioning unit, and which has a number of elements at known distances from each other.

8. The method as set forth in claim 7, wherein said element including a plurality of elements spaced in a triangular relationship.

9. The method as set forth in claim 8, wherein the analysis software moves the beam around each of the elements to determine a center of each of the elements, and the distances between the centers are utilized to determine the distance from the x-ray source spot location to the center of rotation on the object positioning unit.

10. A method of calibrating a computed tomography system including the steps of:
mounting a scan geometry defining tool on a rotating object positioning unit of a computer tomography scanner, said scan geometry defining tool having structure at a known location relative to a center of rotation of the object positioning unit;
directing a beam from an x-ray source of the computed tomography system through the structure of the scan geometry defining tool, analyzing a detected image after absorption of the x-ray from the scan geometry defining tool, and utilizing said analyzed image to determine a distance from an x-ray location to the center of rotation of the object positioning unit;
directing a beam from the x-ray tool at an system performance test standard tool and analyzing a number of electronic and computer performance characteristics, and comparing the analyzed characteristics to expected characteristics to provide feedback on the operation of electronic and computer functions within the computed tomography system; and
system performance test standard tool includes a metal disk of a known size which is scanned by the x-ray source.

11. A computed tomography system comprising:
a scan geometry defining tool mounted on a rotating object positioning unit of a computer tomography scanner, said scan geometry defining tool having structure at a known location relative to a center of rotation of the object positioning unit;
an x-ray source to direct a beam at the structure on the scan geometry defining tool, a computer for analyzing a detected image after absorption of the x-ray from the scan geometry defining tool, and said computer utilizing said analyzed image to determine a distance from an x-ray source spot location to the center of rotation of the object positioning unit; and
the x-ray source also directing a beam at an system performance test standard tool and the computer analyzing a number of electronic and computer performance characteristics, and comparing the analyzed characteristics to expected characteristics to provide feedback on the operation of electronic and computer functions within the computed tomography system, said system performance test standard tool including a metal disk of a known size which is scanned by the x-ray source.

12. The system as set forth in claim 11, wherein distinct tools are utilized as the scan geometry defining tool and the system performance test standard tool.

13. The system as set forth in claim 12, wherein a single tool is utilized to provide the electronic and computer control characteristics.

14. The system as set forth in claim 11, wherein a standard size element is positioned on the object positioning unit along with a component to be scanned, and the standard size element is utilized to provide further feedback on the accuracy of the information provided by the computed tomography system with regard to the component to be scanned.

15. The system as set forth in claim 11, wherein the scan geometry defining tool includes a plate which is to be positioned on the object positioning unit, and which has a number of elements at known distances from each other.

* * * * *